US010281474B2

(12) United States Patent
Regnier et al.

(10) Patent No.: US 10,281,474 B2
(45) Date of Patent: May 7, 2019

(54) METHOD FOR ANALYZING SAMPLES OF BIOLOGICAL FLUID AND APPARATUS FOR PERFORMING THE SAME

(71) Applicant: Novilytic, LLC, West Lafayette, IN (US)

(72) Inventors: Fred Regnier, Carmel, IN (US); JinHee Kim, West Lafayette, IN (US)

(*) Notice: Subject to any disclaimer, the term of this patent is extended or adjusted under 35 U.S.C. 154(b) by 0 days.

(21) Appl. No.: 16/002,798

(22) Filed: Jun. 7, 2018

(65) Prior Publication Data

US 2018/0284129 A1 Oct. 4, 2018

Related U.S. Application Data

(62) Division of application No. 14/814,081, filed on Jul. 30, 2015, now Pat. No. 10,018,635.

(60) Provisional application No. 62/030,920, filed on Jul. 30, 2014.

(51) Int. Cl.
*G01N 33/68* (2006.01)
*G01N 33/543* (2006.01)

(52) U.S. Cl.
CPC ... *G01N 33/6848* (2013.01); *G01N 33/54313* (2013.01)

(58) Field of Classification Search
None
See application file for complete search history.

(56) References Cited

U.S. PATENT DOCUMENTS

| 8,440,797 | B2 | 5/2013 | Watanabe et al. |
| 8,592,347 | B2 | 11/2013 | Frendeus |
| 8,686,122 | B2 | 4/2014 | Bieniarz et al. |
| 10,018,635 | B2 * | 7/2018 | Regnier ........... G01N 33/54313 |
| 2002/0150926 | A1 | 10/2002 | Jindal et al. |
| 2006/0070954 | A1 | 4/2006 | Martosella et al. |
| 2009/0236519 | A1 | 9/2009 | Viberg et al. |
| 2010/0273178 | A1 | 10/2010 | Regnier |
| 2013/0011925 | A1 | 1/2013 | Gilar et al. |

FOREIGN PATENT DOCUMENTS

EP          1300679 A2    9/2003

OTHER PUBLICATIONS

Chester: Recent Developments in HPLC Stationary Phases; Analytical Chem.; vol. 85, pp. 579-589; Nov. 2, 2012, p. 580 col. 1; para. 5; and, passim.
Walles el. al.: Monitoring of Drugs and Metabolites in Whole Blood by Restricted Access Solid Phase Microextraction Couple to LC-MS; J_ Chromatography, vol. 1025 pp. 85-92 (2004); Abs.

* cited by examiner

*Primary Examiner* — Blaine Lankford

(57) ABSTRACT

The present invention relates to methods for continuous or near-continuous separation and purification of samples, particularly biological samples, to reduce the number or volume of non-targeted analytes in those samples to enable improved mass spectrometric analysis of analytes of interest, and apparatuses for conducting those methods, utilizing a transport agent with a core domain and a binding domain, the transport agent exceeding 200 kiloDaltons or 10 nm, and the binding domain targeted to the analytes of interest, in conjunction with size-exclusion based chromatography to separate the transport agent-analyte of interest complex from non-targeted analytes that are not bound, or are only non-specifically bound, to the transport agent.

10 Claims, 12 Drawing Sheets

METHOD FOR ANALYZING SAMPLES OF BIOLOGICAL FLUID AND APPARATUS FOR PERFORMING THE SAME

CROSS-REFERENCES TO RELATED APPLICATIONS

This Application is a divisional of, and incorporates in its entirety, U.S. application Ser. No. 14/814,081, Method for Analyzing Samples of Biological Fluid and Apparatus for Performing the Same, filed Jul. 30, 2015, which is a non-provisional of, and incorporates in its entirety, U.S. Application No. 62/030,920, Method for Analyzing Samples of Biological Fluid and Apparatus for Performing the Same, filed Jul. 30, 2014. This application is further related to a Patent Cooperation Treaty Application No. PCT/US2015/042952, filed on Jul. 30, 2015, titled Method for Analyzing Samples of Biological Fluid and Apparatus for Performing the Same.

STATEMENT REGARDING FEDERALLY SPONSORED RESEARCH OR DEVELOPMENT

The present invention was made with government support under Grant No. GM116663-01, awarded by the National Institute of Health (NIH). The Government has certain rights in this invention.

TECHNICAL FIELD

This invention teaches versions of methods and apparatuses for the analysis of biological samples. In the past, various methods have been used to qualitatively observe or quantitatively measure different targets within a biological sample. For example, it is known to the art to analyze proteins in histological sections and other cytological preparations using the techniques of histochemistry, immunohistochemistry (IHC), or immunofluorescence. Analysis of proteins in biological samples may also be performed using solid-state immunoassays, for example, using the techniques enzyme-linked immunological assays, radio immunological assays, and western blots. Typical supports used in these solid-state assays include microtiter plates, magnetic beads, and glass particles in radio-immunological assay kits.

Many currently-known techniques detect only a few targets at one time (such as, IHC or fluorescence-based western blots where number of targets detectable is limited by the fluorescence-based detection system) in a single sample. Additional analysis of targets may require the use of additional biological samples from the source, limiting the ability to determine relative characteristics of the targets such as the presence, absence, concentration, or the spatial distribution of multiple biological targets in the biological sample. Moreover, in certain instances, a limited amount of sample may be available for analysis or the individual sample may require further analysis.

It is also known to the art to conduct such analysis employing liquid chromatography (LC), particularly high-performance liquid chromatography (HPLC) coupled with mass spectrometry (LC-MS). This method can offer increased sensitivity and selectivity. However, LC and HPLC as traditionally practiced suffer a number of drawbacks. First, LC and HPLC require long separation times, making these techniques generally unsuitable where rapid analysis is desired. Further, the stationary phase of LC and HPLC, and other chromatographic techniques known to the art, must be continually refreshed, limiting the flow rate, increasing expense, and further reducing the suitability of these techniques where high-volume analysis is required. Also, biological samples subjected to LC and HPLC often contain so many potential interfering substances, such as analytes other than analytes of interest, that if the elution were subjected to mass spectrometry, an unmanageable number of peaks would be read. Thus, samples subjected to LC or HPLC must often be further refined or separated through subsequent operations prior to mass spectrometric (MS) analysis, further increasing time and cost.

One further drawback to some LC and HPLC techniques known to the art, particularly reverse-phase-based chromatography, is that biological agents are separated based on general properties that are shared by a large number of molecular species. For example, most proteins, lipids, and amino acids, as well as some categories of other molecules, bear multiple —CH— or —CH$_2$— groups. Common techniques like reverse-phase chromatography (RPC) that separate by hydrophobic interaction will select all molecules in this broad category. For further example, within a plasma sample, hundreds of thousands of substances exist that would be retained by an RPC column. Ion exchange chromatography and size exclusion chromatography, as generally used in the art, similarly separate based upon common general properties, with the result that absent further sample refinement, an undesirably high number of biological agents are partitioned and eluted for MS analysis. This poses a problem when the desired application is rapid or high-volume analysis of a complex sample, such as a whole blood or plasma sample. Whole blood, for example, contains hundreds of thousands of molecular species that would be typically separated into approximately 200 chromatographic peaks, each peak sweeping in hundreds of potential components into a detector, if the sample were analyzed solely through LC or HPLC methods known to the art. Mass spectrometers can handle a mixture of a hundred components simultaneously, but cannot handle thousands. Chromatographic methods known to the art are therefore poorly suited for rapid or high volume analysis of complex samples.

It is known to the art to begin the process of analysis of biological samples, particularly whole blood, through use of a plasma separator device. A representative plasma separator device is described, for example, in U.S. Pat. No. 4,839,296. It is also known in the art to use quantitative separation, purification, or analysis techniques such as LC, MS, LC-MS, and HPLC-MS on plasma separated by use of a plasma separation device (PSD), as described by U.S. Patent Publication No. 2012-20318971. However, even in combination with a PSD, these techniques as currently employed fail to achieve time, cost, and efficiency savings equal to the methods and apparatuses described herein.

SUMMARY

Accordingly, it is an object of the present invention to provide methods of assaying biological samples for the levels, amounts, or concentrations of analytes of interest without the need for lengthy and labor-intensive preparation steps prior to analysis, and for such methods to work more rapidly and at better flow rates than current LC, LC-MS, HPLC, or HPLC-MS techniques allow. It is further an object of the present invention to provide a chromatographic technique that targets analytes of interest and isolates them quickly from a whole biological sample, such as a whole blood sample, such that MS can be performed to qualitatively and quantitatively analyze the isolated analytes.

In general terms, versions of the method of the present invention involve the following steps:

(a) providing a sample for analysis, such as, by way of example, using a PSD to isolate a plasma aliquot from whole blood;

(b) selecting at least one affinity transport particles ("ATPs"), which generally comprise a particle of larger than approximately 10 nm, and preferably larger than 50 nm in diameter with a relatively large core domain and a binding domain on the outer surface suitable for binding to one or more analytes desired to be analyzed;

(c) adding selected ATPs to the sample, either as a separate step, or within the collection portion of a PSD, or within an aqueous buffer or other solute in which the sample is or will be present, to create a sample mixture including both analytes (if any are present in the sample) and selected ATPs;

(d) in at least one location where the selected ATPs and analytes desired to be analyzed are likely to encounter each other within the sample mixture, provide conditions favorable for the analytes of interest to bind to the binding domains of one or more of the ATPs;

(e) load the sample mixture into an apparatus comprising:

(i) one or more stripping columns, the stripping column including a stationary phase comprising a size-restricted access sorbent of greater than approximately 1 um particle diameter, configured to retain agents smaller than approximately 200 kiloDaltons in molecular size, such that most biological agents not bound to an ATP and biological agents only weakly or non-specifically bound to an ATP are retained by the size-restricted sorbent;

(ii) at least one disassociating portion, preferably fluidly connected to the stripping column, the disassociating portion configured to host conditions suitable to disassociate analytes of interest from ATPs and preferably also configured to separate out disassociated ATPs through the tubular pinch effect; and (iii) optionally, at least one enriching column fluidly connected to the disassociating portion, the enriching column configured to maintain conditions that disfavor analytes of interest rebinding to ATPs and also configured to chromatographically separate analytes of interest from ATPs;

(f) move the sample mixture through the stripping column at a speed selected to allow substantially all biological agents not bound to an ATP to bind to said size-restricted access sorbent;

(g) establishing conditions in the disassociating portion configured to disassociate one or more of the analytes of interest from the ATPs, such as, by way of example, adding heat or lowering pH;

(h) moving the sample mixture through the disassociating portion at a speed selected to allow the analytes of interest to substantially disassociate from the ATPs;

(i) establishing or maintaining conditions in the enriching column disfavoring rebinding of analytes of interest to ATPs;

(j) moving the sample mixture through the enriching column at a speed selected to allow chromatographic separation of analytes of interest from ATPs, preferably substantially the same speed at which the sample mixture moved through the stripping column; and (h) analyzing the elution from the enriching column through materials analysis methods known to the art, such as, by way of example, mass spectrometry, fluorescence, and UV-Vis, to qualitatively or quantitatively to determine the presence or relative amount of analytes of interest.

In another embodiment, the method of the present invention comprises the following steps:

(a) providing a sample for analysis, such as, by way of example, using a PSD to isolate a plasma aliquot from whole blood;

(b) selecting one or more ATPs generally comprising particles of larger than approximately 10 nm in diameter and containing a core domain and a binding domain on the outer surface, the binding domain selective to bind to at least one analyte of interest;

(c) adding selected ATPs to the sample, either as a separate step, or within the collection portion of a PSD, or within an aqueous buffer or other solute in which the sample is or will be present, to create a sample mixture including both analytes of interest (if any are present in the sample) and selected ATPs;

(d) in at least one location where the selected ATPs and analytes of interest are likely to encounter each other within the sample mixture, providing conditions favorable for the analytes of interest to bind to the binding domains of one or more of the ATPs;

(e) loading the sample mixture into an apparatus comprising one or more stripping columns, each stripping column comprising a stationary phase comprising a size-restricted access sorbent of greater than approximately 1 um particle diameter configured to retain agents smaller than approximately 200 kilodaltons in molecular size, such that most biological agents not bound to an ATP, and biological agents only weakly or non-specifically bound to an ATP, are retained by the size-restricted sorbent;

(f) moving the sample mixture through the stripping column at a speed selected to allow substantially all biological agents not bound to an ATP to bind to said size-restricted access sorbent;

(g) analyzing the elution from the stripping column through materials analysis methods known to the art, such as, by way of example, mass spectrometry, fluorescence, and UV-Vis, to qualitatively or quantitatively to determine the presence or relative amount of analytes of interest.

The present invention further relates to an apparatus for analyzing complex mixtures. In general terms, versions of the apparatus of the present invention generally comprise at least one stripping column, the stripping column including a mobile phase and a stationary phase. The stationary phase comprises a size-restricted access sorbent configured to retain agents smaller than about 50 nm or 200 kiloDaltons, which would include most or all biological agents not bound to an ATP, and also to retain agents only weakly or non-specifically bound to an ATP. In preferred embodiments, apparatus further includes at least one disassociating portion, preferably fluidly connected to the stripping column, the disassociating portion hosting conditions suitable to disassociate analytes of interest from ATPs; and, optionally, at least one enriching column fluidly connected to the disassociating portion, the enriching column configured or configurable to chromatographically separate the analytes disassociated from the ATP.

Versions of the methods of the present invention preferably employ a sample prepared from a plasma separation device, or PSD, which comprises a device that separates and aliquots a plasma sample of predetermined volume from a whole blood sample of sufficient size applied to the surface of the PSD. A PSD generally comprises a removable holding member, a blood introducing member in the holding member, a spreading layer member in communication with the blood introducing member, a semi-permeable separation member in communication with the spreading layer member, and a collection reservoir of defined volume in communication with the semi-permeable separation member, wherein when a whole blood sample is deposited on the blood introducing member, plasma from the sample passes through the spreading layer member to the separation member, is separated by the separation member, and is collected in a pre-determined volume by the collection reservoir. The collection reservoir may optionally further contain or comprise an absorptive material element, which absorbs substantially all of a collected plasma sample. The collection reservoir may be removed for convenient isolation of the collected plasma sample. The collected plasma sample may then be transferred to a preparation vessel for further processing, or, optionally, an absorptive material element or "collection disc" that has substantially absorbed a collected plasma sample may be so transferred. A PSD may optionally be used for collection of other liquid or liquefied biological samples, including, for example, blood components, saliva, semen, cerebrospinal fluid, urine, tears and homogenized or extracted biosamples (i.e. from a whole organism, organ, tissue, hair, or bone).

These and other advantages are provided in the methods described below, and still further advantages to the methods claimed herein will be apparent to one skilled in the art.

DETAILED DESCRIPTION

Figure 1:
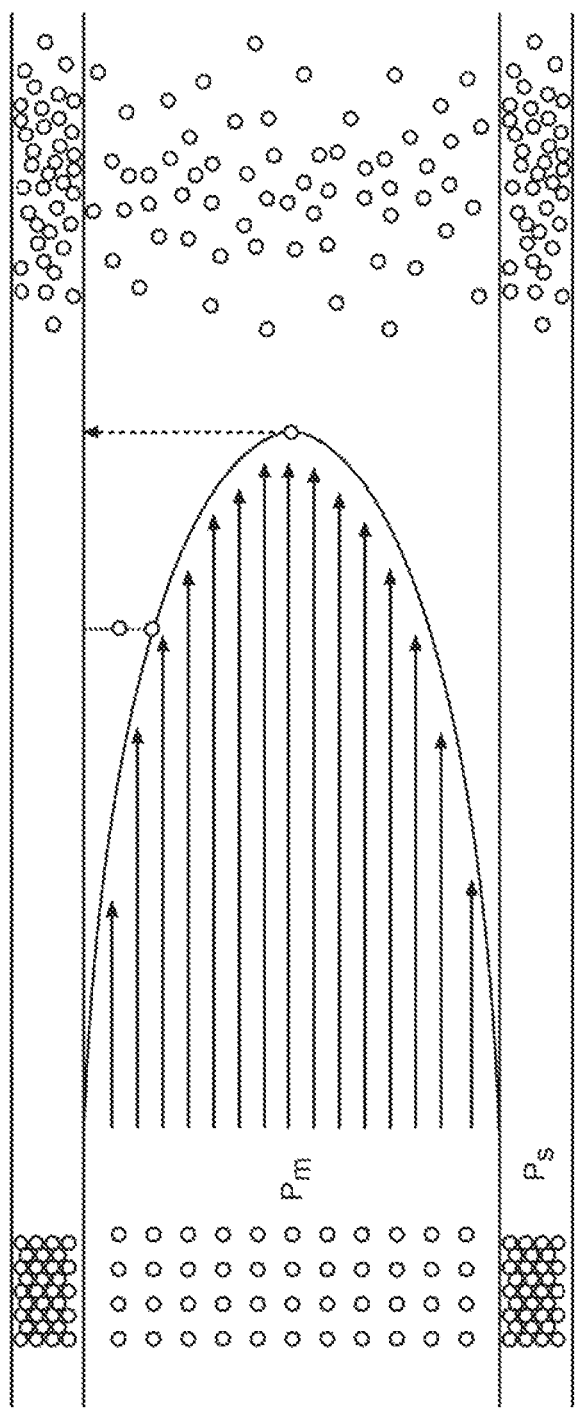
FIG. 1 is shows exemplary laminar flow partitioning between the mobile phase and stationary phase of within the apparatus of one version of the present invention.
Figure 2A:
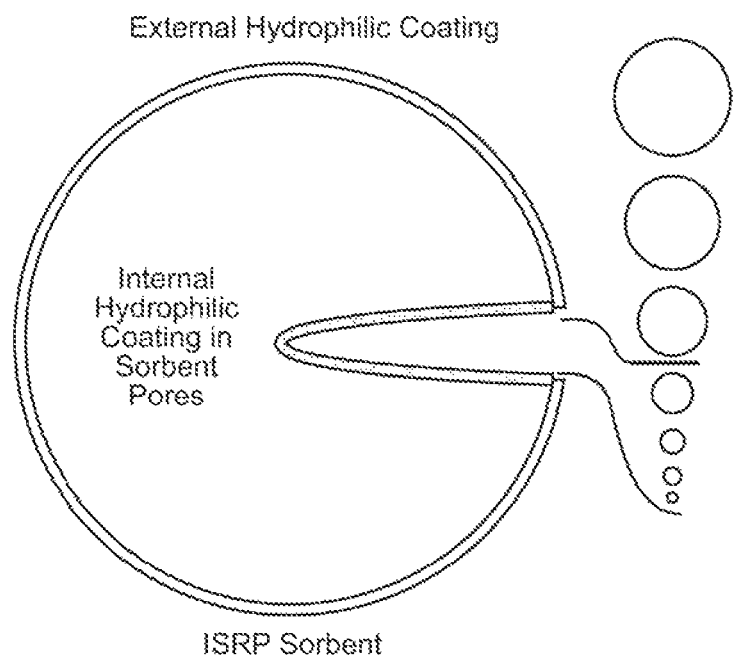
FIG. 2A is an exemplary illustration of one embodiment of a size-restricted sorbent within the scope of versions of the present invention.
Figure 2B:
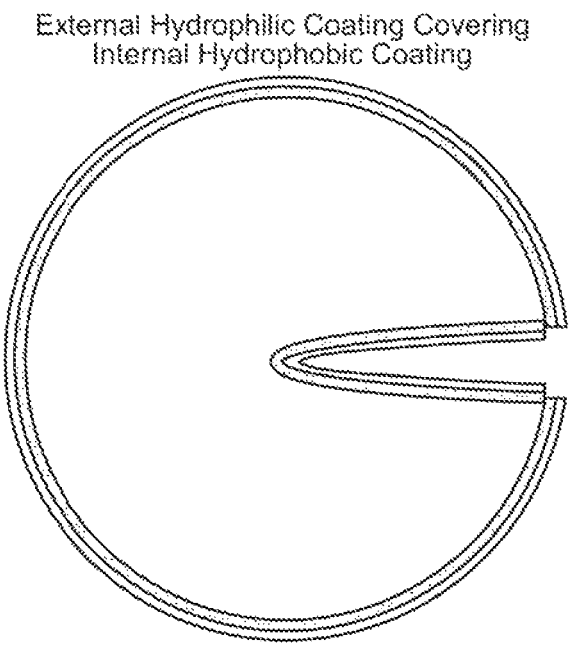
FIG. 2B an illustration of a second embodiment of a size-restricted sorbent within the scope of versions of the present invention.
Figure 3A:
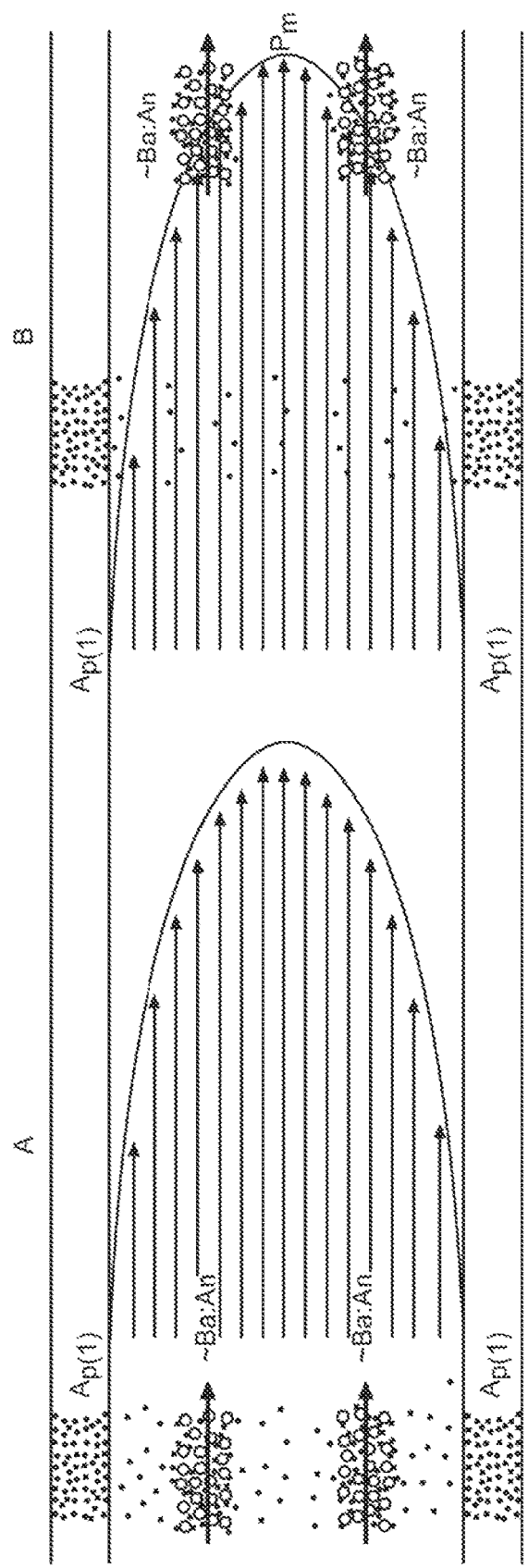
FIG. 3A is an exemplary illustration of the tubular pinch effect within a capillary tube disassociating portion of embodiments of the present invention.
Figure 3B:
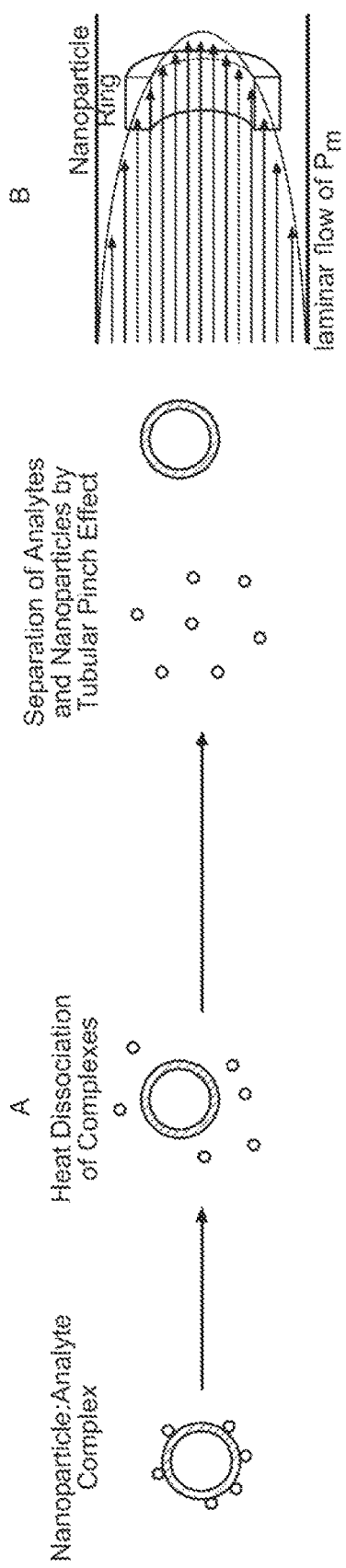
FIG. 3B is an exemplary illustration of the partitioning of disassociated ATPs from disassociated analytes of interest due to the tubular pinch effect in an embodiment of the present invention.
Figure 4A:
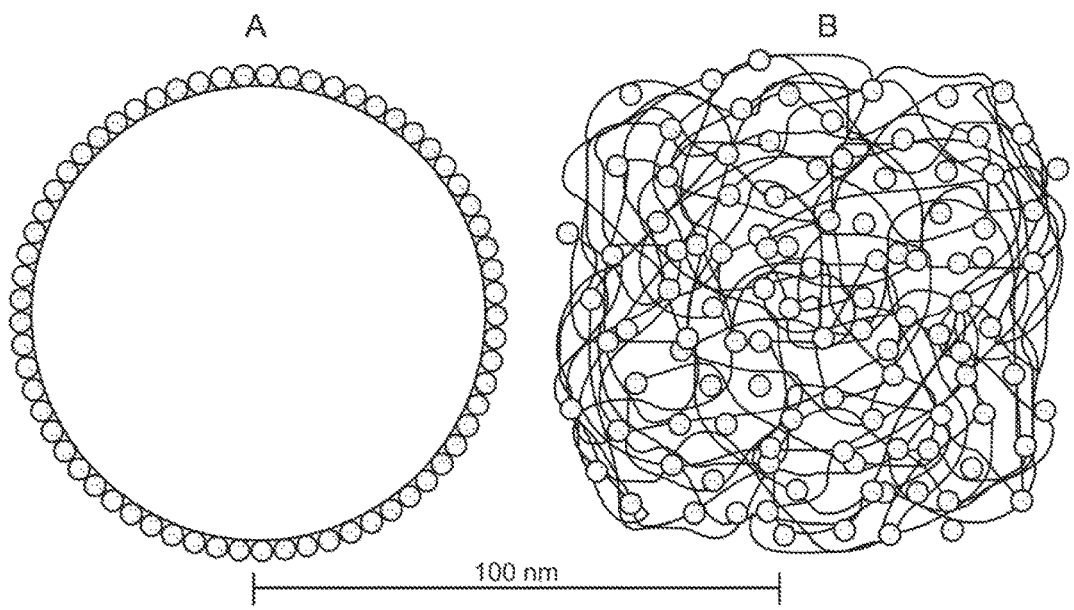
FIG. 4A is an exemplary diagram of proteins bound to the binding domain of two different ATPs in embodiments of the present invention.
Figure 4B:
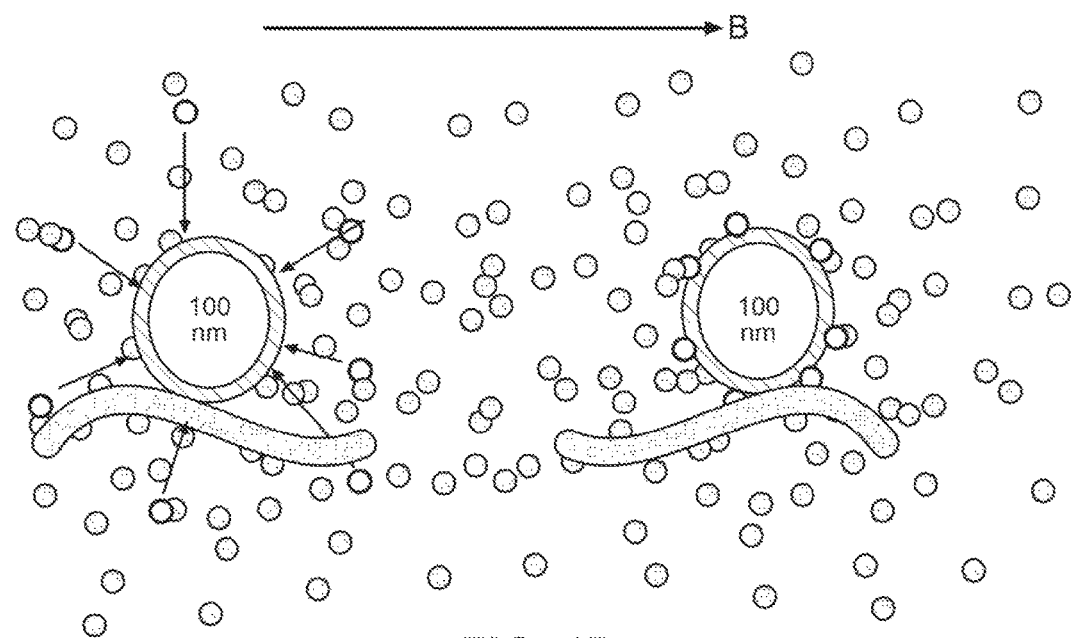
FIG. 4B is an exemplary diagram demonstrating the binding effect of an ATP with targeted analytes in one embodiment of the invention.
Figure 5A:
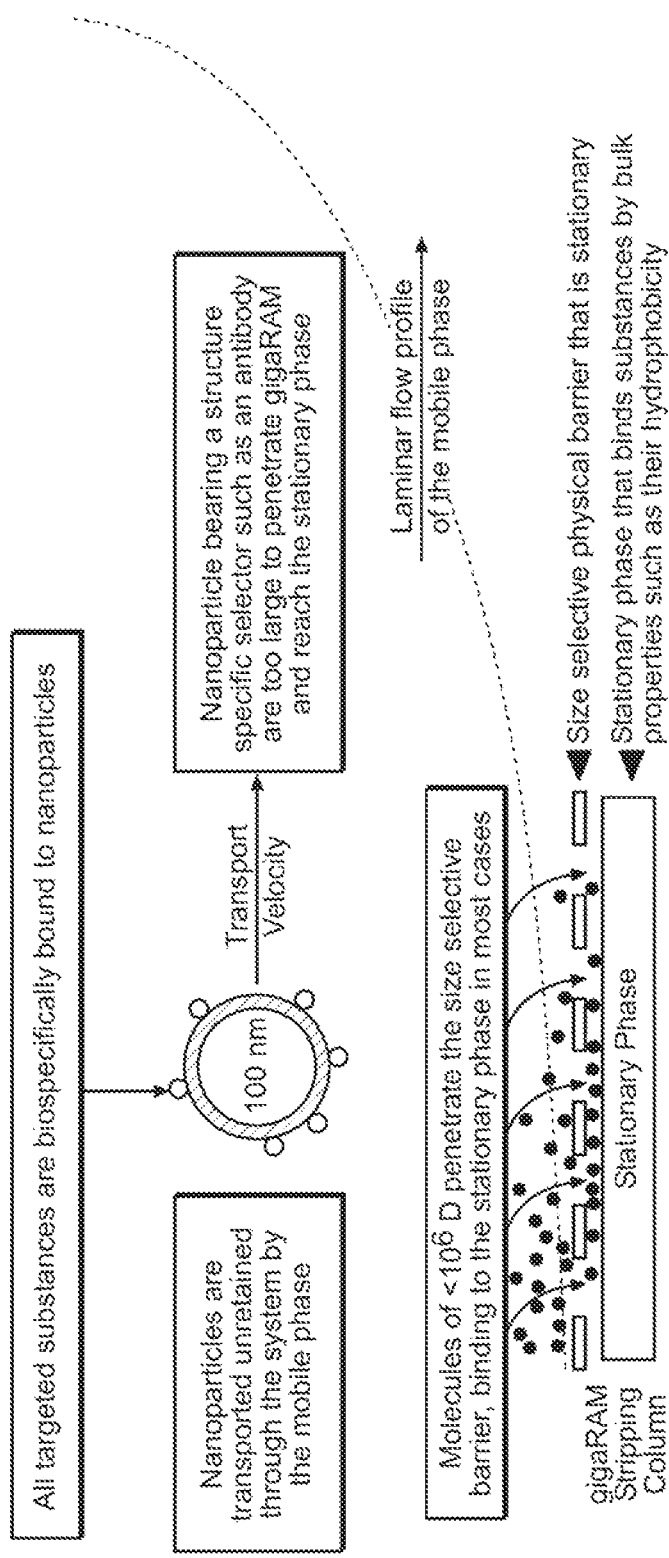
FIG. 5A is a flow chart illustrating steps in the passage of a sample passing through a stripping column, and undergoing size-restricted separation in one embodiment of the present invention.
Figure 5B:
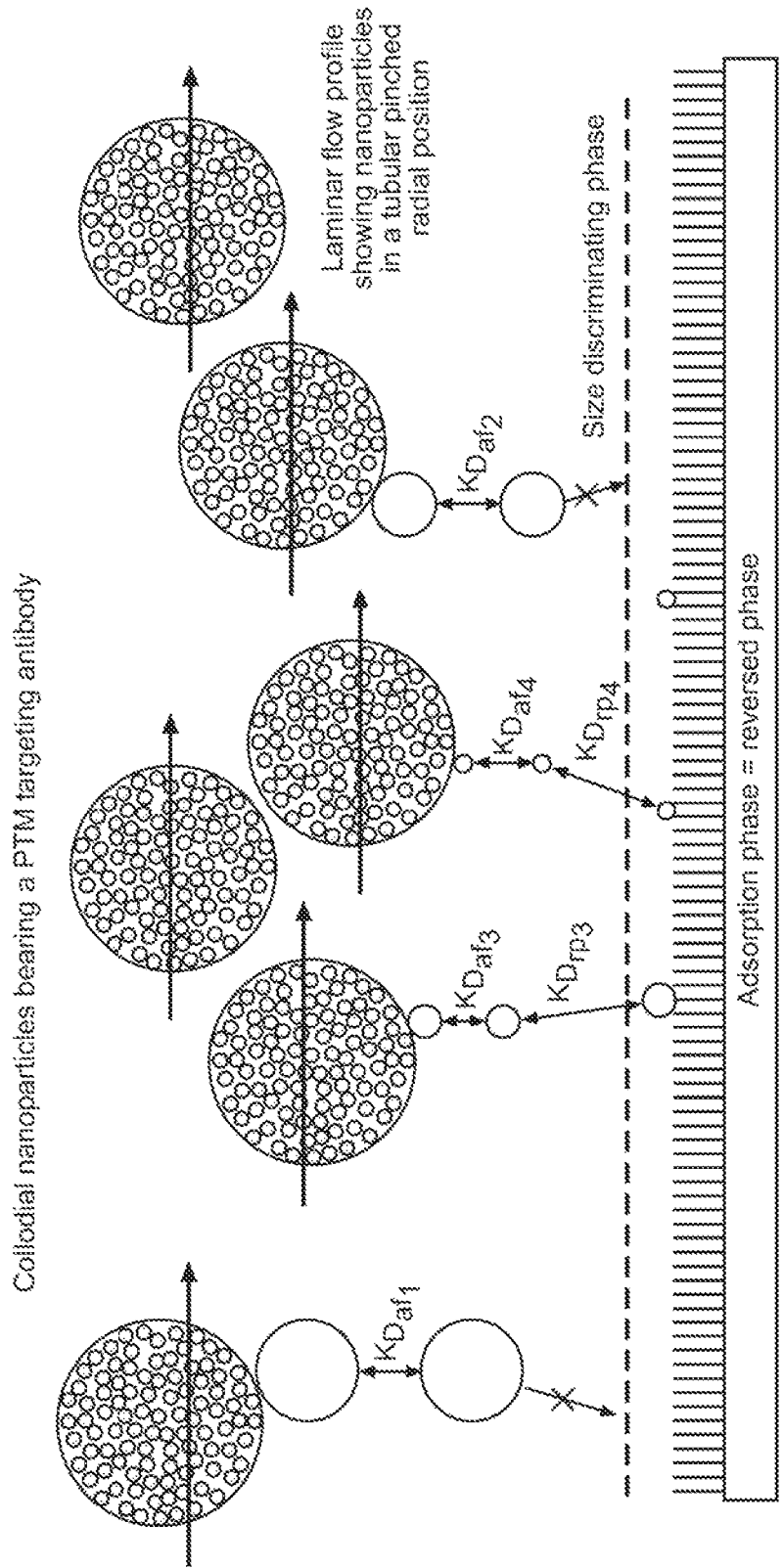
FIG. 5B is a flow chart illustrating steps in the passage of a sample passing through a stripping column and undergoing size-restricted separation in another embodiment of the present invention.

While the composition and use of various versions of the method of the present invention are discussed in detail below, it should be appreciated that the present invention includes a variety of particular embodiments that can be employed in a wide range of specific contexts. The specific versions and embodiments discussed herein are merely illustrative of the manners in which the methods of the present invention can be composed and used, and do not serve to limit the scope of the invention.

Specifically, as will be appreciated by one skilled in the art, various iterations and embodiments of the methods described below are presented, however, the invention is not limited to these iterations or embodiments, or to the specific order of steps presented herein. Variations in the number and order of steps, addition of other steps, and combinations of aspects of the various embodiments herein, all fall within the scope of the claimed invention.

Terms used herein have meaning as commonly understood by one of ordinary skill in the relevant art, unless otherwise specifically defined herein. While the terms herein are used to describe particular embodiments and versions of the present invention, they are not intended to limit the scope of the invention except as specifically stated in the claims.

An "analyte" or "analyte of interest" according to versions of the present invention refers to compounds or components desired to be measured in a sample. Analytes can be any compound, component, or class of compounds that are or may be found in biological fluids, including specifically and preferably whole human blood or whole animal blood. Analytes may further comprise pharmaceutical or therapeutic agents, including drugs. Preferably, analytes comprise drugs, metabolites, biopharmaceuticals, and proteins. Analytes further refers to isotopes, isomers, and analogs of all of the above. "Analytes" or "analytes of interest" refer to analytes for which a sample is to be analyzed quantitatively or qualitatively, without regard to whether those analytes actually exist in the sample.

A "sample" according to versions of the present invention refers to any quantity of matter that is liquid or which has been liquefied that is suspected of containing a quantity of one or more analytes of interest detectable by mass spectrometric analysis. Samples may include, by way of illustration, cells or cell cultures, organs, organ pieces or organ cultures, whole blood, plasma, serum, semen, hair, muscle, bone, saliva, tears, urine, feces, cerebrospinal fluid, or unknown substances suspected to contain detectable quantities of one or more analytes. Preferably, a sample refers to a quantity of whole blood, and, preferably, of a quantity of human blood, and, most preferably a quantity of human blood plasma. It would be understood by one skilled in the art that since ATPs within the scope and spirit of this invention are generally colloidal solids, the "sample mixture" referred to herein may comprise either a solution including ATPs, or, preferably, a colloidal suspension including ATPs.

A "plasma separation device" or "PSD" refers to a plasma separation device for use in some versions of the present invention. It will be appreciated that the PSD can separate, aliquot, and collect a plasma sample of pre-determined volume from a whole blood sample, saving time, labor, and effort compared to other methods of sample collection and preparation. Optionally, a PSD may, as described herein, be loaded with one or more internal standards, derivatizing agents, digesting agents, or ATPs prior to, during, or after sample collection by the PDS within the scope and spirit of various versions of the present invention.

A PSD may optionally be pre-loaded with a derivatizing agent by, prior to collection of a sample in the PSD, loading a desired quantity of derivatizing agent within the collection reservoir or, optionally, an absorptive material element of the PSD. It will be appreciated by one skilled in the art that the PSD may be pre-loaded with a derivatizing agent prior to use of the PSD, without respect to when the PSD is intended to be used to collect a sample. As will be appreciated by one skilled in the art, the effective shelf life of such a pre-loaded PSD will depend on the identity, stability, and rate of deterioration of the selected derivatizing agent.

A PSD may be optionally be pre-loaded with an internal standard by, prior to collection of a sample in the PSD, loading a desired quantity of internal standard within the collection reservoir, semi-permeable member, or, optionally, absorptive material element of the PSD. It will be appreciated by one skilled in the art that the PSD may be pre-loaded with an internal standard at any time prior to use, without respect to when the PSD is intended to be used to collect a sample. As will be appreciated by one skilled in the art, the effective shelf life of such a pre-loaded PSD will depend on the identity, stability, and rate of deterioration of the selected internal standard. Optionally, the blood holding member or semi-permeable member may be pre-loaded with an internal standard by treating or impregnating such members of the PSD with a desired amount of internal standard in liquid or solid form.

A PSD may optionally be pre-loaded with a digesting agent by, prior to collection of a sample in the PSD, loading a desired quantity of digesting agent within the collection reservoir or, optionally, an absorptive material element of the PSD. It will be appreciated by one skilled in the art that the PSD may be pre-loaded with a digesting agent prior to use of the PSD, without respect to when the PSD is intended to be used to collect a sample. As will be appreciated by one skilled in the art, the effective shelf life of such a pre-loaded PSD will depend on the identity, stability, and rate of deterioration of the selected digesting agent. Preferably, the digesting agent is trypsin or a trypsin nanoparticle.

A PSD may optionally be pre-loaded with one or more ATPs by, prior to collection of a sample in the PSD, loading a desired quantity of one or more ATPs within the collection reservoir or, optionally, an absorptive material element of the PSD. It will be appreciated by one skilled in the art that the PSD may be pre-loaded with one or more ATPs prior to use of the PSD, without respect to when the PSD is intended to be used to collect a sample. As will be appreciated by one skilled in the art, the effective shelf life of such a pre-loaded PSD will depend on the identity, stability, and rate of deterioration of the selected ATPs.

An "internal standard" as used herein refers to a substance added in a known amount to a sample, wherein a mass spectrometric signal of the known internal standard can be compared to the mass spectrometric signal, if any, of analytes of interest within the sample, and, through this comparison, the presence and amount of analytes of interest can be determined. An ideal internal standard is a substance with a highly similar, and, if possible, identical chemical structure to the analyte of interest, that differs only by the presence of heavy atoms at specific sites in the internal standard. For instance, a deuterium isotope of VD, in which a deuterium atom is substituted for a hydrogen atom, is an appropriate internal standard for VD. Although the analyte of interest and internal standard differ in mass and are recognized individually by mass spectrometry, their fragmentation patterns and relative yields of fragment ions are substantially identical. Internal standards preferably comprise one or more isotopically labeled analytes of interest.

"Isotopic labeling," "isotopically labeled," "coding," or "coded" refers to the replacement of one or more atoms within an internal standard molecule with an atom containing the same number of protons and electrons, but varying numbers of neutrons. Isotopic labels produce a mass shift in the isotopically labeled molecule relative to the unlabeled molecule when analyzed by mass spectrometric techniques, wherein the amount of the unlabeled molecule can be determined by comparison of its mass spectrometric signature with the mass spectrometric signature of the labeled internal standard molecule. Since the gas phase fragmentation pattern produced during mass spectrometry is independent of isotope labeling, use of isotopically labeled internal standards is appropriate for methods of the present invention. Suitable isotopic labels include, by way of example, deuterium ($^2$H), $^{13}$C, and $^{15}$N. For example, a 25-hydroxy vitamin D3 molecule isotopically labeled with deuterium would be 3 atomic mass units (amu) greater than an unlabeled 25-hydroxy vitamin D3 molecule, resulting in a detectable mass shift differentiating the 25-hydroxy VD3 molecule and its isotopically labeled internal standard when both are analyzed through MS. An isotopic label can be incorporated at one or more positions in a molecule, and one or more isotopic labels can be used on the same isotopically labeled molecule.

"Analyzing" refers to employing appropriate techniques to determine the presence or absence, and, optionally, amount or concentration, of one or more analytes of interest. Specifically, analyzing refers to employing quantitative analytical techniques to measure the presence, amount, or concentration of one or more analytes of interest quantitatively or qualitatively through materials analysis techniques known to the art. Such techniques include, but are not limited to, mass spectrometry, fluorescence, and Uv-Vis. Preferably, "analyzing" or "analysis" refers to mass spectrometry.

"Mass spectrometry" or "MS" refers to a method for analysis of compounds and fragments thereof by their mass. MS includes methods of filtering, detecting, and measuring ions based on their mass-to-charge ration (m/z). As will be appreciated by one skilled in the art, MS generally includes: (1) ionizing a compound to be analyzed to form charged compounds; (2) detecting the molecular weight of the charged compounds and fragments thereof; and (3) calculating a mass-to-charge ratio for the detected charged ions. Ionization may occur by any suitable means, as will be apparent to one skilled in the art. Suitable means of ionization include, by way of illustration, atmospheric pressure chemical ionization, atmospheric pressure photoionization, inductively coupled plasma, field desorption, laser diode thermal desorption, electrospray ionization, fast atom bombardment, matrix-assisted laser desorption ionization ("MALDI"), or surface-enhanced laser desorption ("SELDI"). Ion detection may also be performed by any suitable means, as will be apparent to one skilled in the art.

By way of example, detection may be performed in positive ion mode, or, alternatively, negative ion mode. Detection may if desired be performed using selective ion monitoring or multiple reaction mode ("MRM"). In some embodiments, parent daughter ion transition monitoring (PDITM), selective reaction monitoring (SRM), or MRM of derivatized analytes is performed using a triple quadropole MS platform.

The "lower limit of quantification" refers to the point where MS measurements become quantitatively meaningful. It is the lowest point at which analyte response is identifiable, discrete, and reproducible with a relative standard deviation of less than 20% and accuracy of greater than 80%. The "limit of detection" refers to the point at which the value measured using mass spectrometry is equal to or less than the uncertainty associated with that value, and is defined as three times the relative standard deviation of the mean at zero concentration.

As used herein "chromatography" generally refers to a process in which a chemical mixture carried by a liquid or gas is separated into components as a result of differential distribution of the chemical entities as they flow around or over a stationary liquid or solid phase. LC refers to a process of selective retardation of one or more components of a fluid solution as the fluid uniformly percolates through a column of finely divided substance, or through capillary passageways. The retardation results from the distribution of the components of the mixture between one or more stationary phases and the bulk fluid (or mobile phase), as this mobile phase moves relative to the stationary phases. Examples of LC include reverse phase liquid chromatography, high performance liquid chromatography, turbulent flow liquid chromatography, and high throughput liquid chromatography. Affinity chromatography is a form of LC achieved by passing a sample through a stationary phase comprising a packed column or bed of insoluble particles, typically one to fifty um in size. The stationary phase comprises immobilized binding agents (~Ba) that selectively capture agents (A) based on their structure during flow of a solute mobile phase containing A through the stationary phase, forming a ~Ba:A complex. The ~Ba:A complex associates and disassociates with the stationary phase in equilibrium with the mobile phase, resulting in differing agents proceeding through the LC column at different effective speeds, with agents that demonstrate greater affinity to the stationary phase taking longer to pass than agents with less affinity to the stationary phase. This separation facilitates later analysis, such as MS analysis.

An ATP within the scope and spirit of the present invention refers to an agent with an atomic weight equal to or exceeding approximately 500 kiloDaltons or, in the case of colloidal particles, a diameter exceeding 10 nm, or preferably 50 nm, that comprises a core domain and a binding domain. In general terms, the ATP acts as a transport agent that sequesters analytes of interest, preferably by binding, based on their structure or functional groups and prevents those bound analytes to from contacting, and thus from being retained by, size-restricted sorbents in the stripping column. Thus, analytes of interest bound to the ATPs during transit through a stripping column will proceed through the remainder of the methods described herein, while substantially all analytes not bound to ATPs, or only weakly or non-specifically bound to ATPs, will be retained (as in, for example, hydrophobic interaction, electrostatic interaction, reversed phase chromatography, and size-mediated filtration) by the size-restricted access sorbent of the stripping column and will not proceed through the remainder of the method, and specifically will not be subjected to analysis. The ATPs, used in conjunction with the other steps of the methods and apparatuses disclosed herein, thus allow relative enrichment and purification of selected analytes at generally high speed compared to traditional methods.

Figure 8:
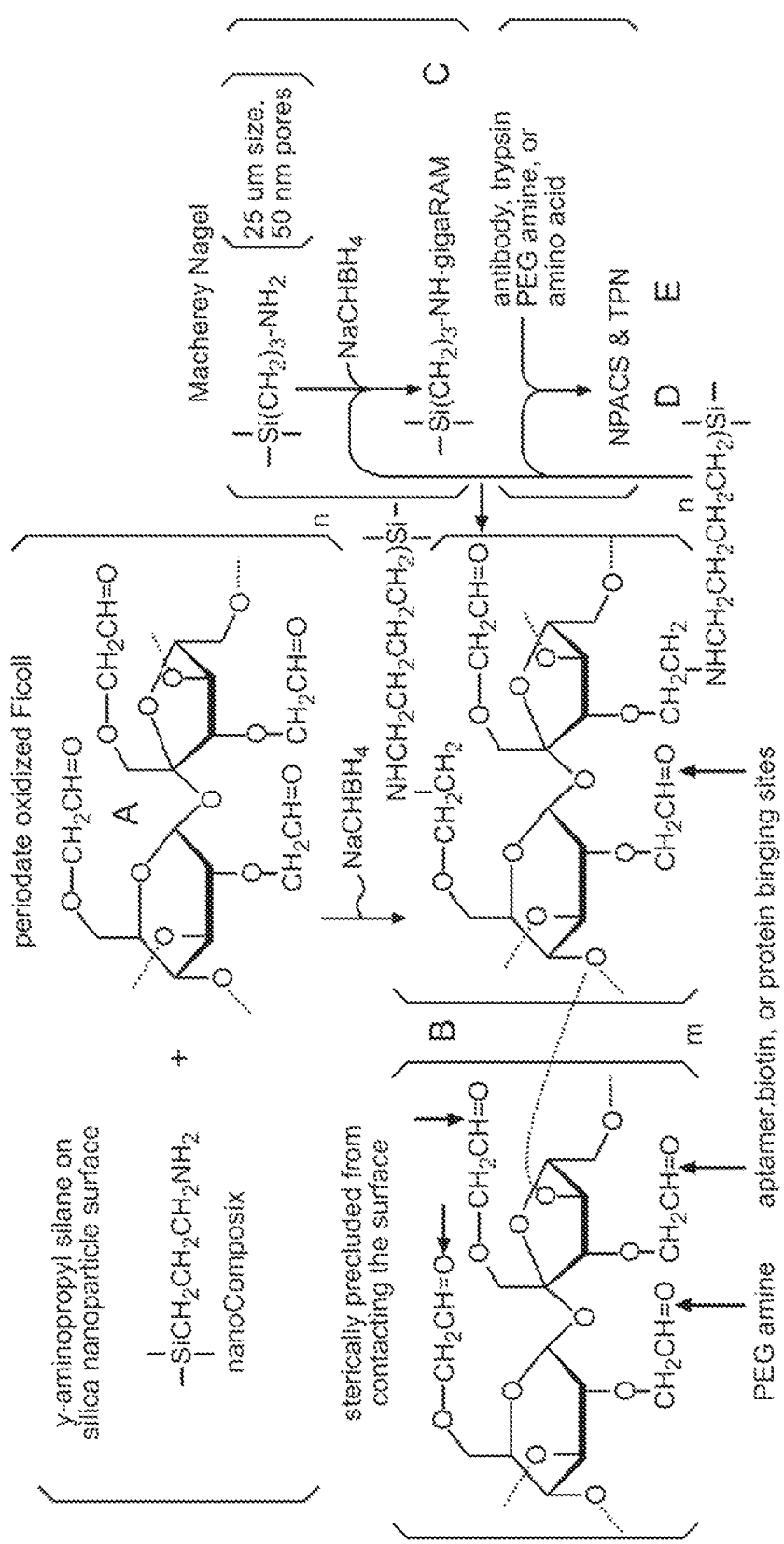
FIG. 8 is an illustrative diagram of synthesis of one ATP particle suitable for use with versions of the present invention.
Figure 9:
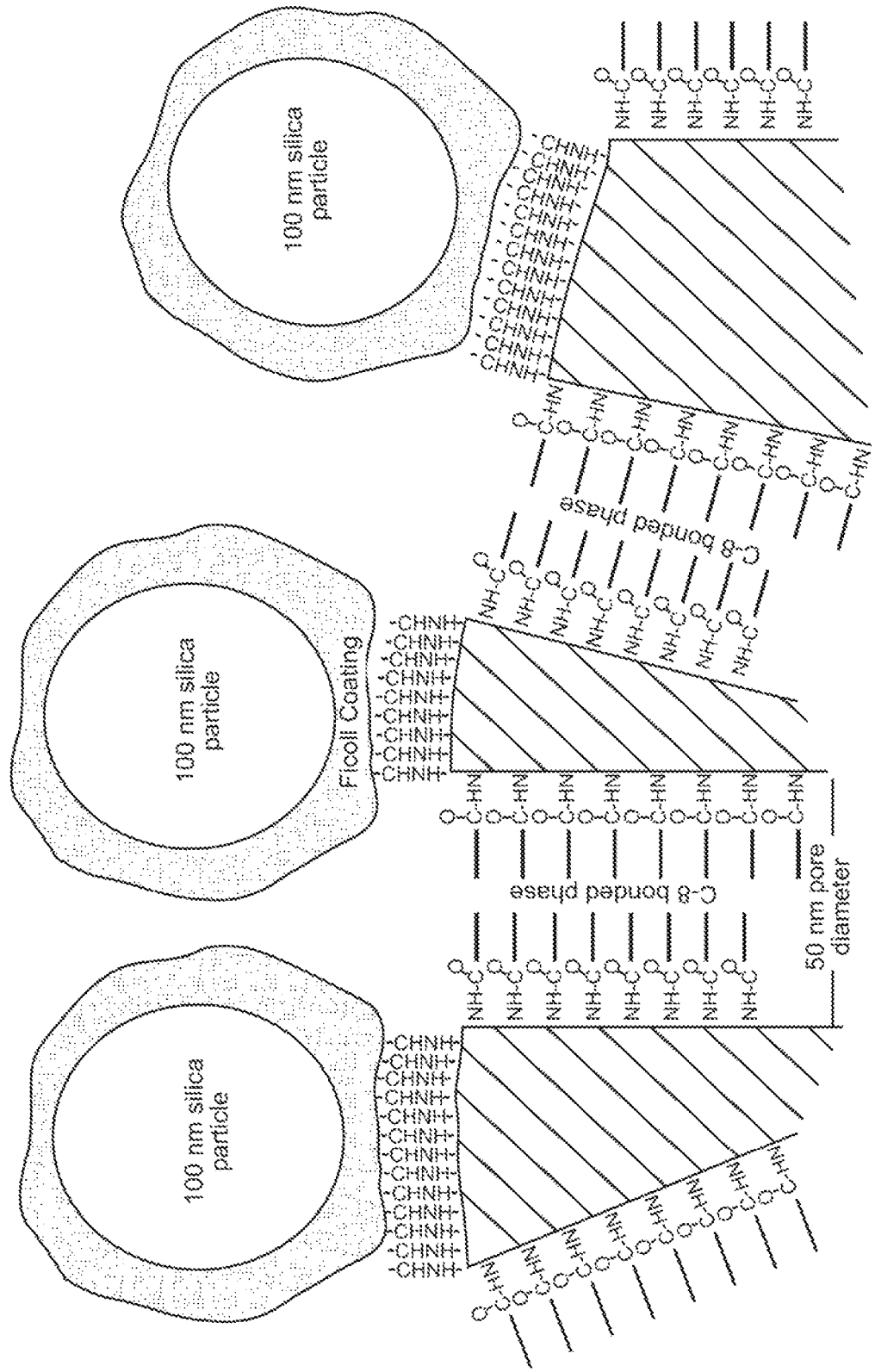
FIG. 9 is a cross-sectional illustrative diagram of one ATP suitable for use with versions of the present invention.

ATPs can generally be synthesized as coated silica particles, binding agent derivatized Ficoll, binding agent derivatized polysaccharide, including dextran, binding agent derivatized hydrophilic polymers, modified immunoglobulin M, binding agent derivatized organic nanoparticles, binding agent derivatized latex nanoparticles, or binding agent derivatized inorganic nanoparticles. Synthesis of one ATP suitable for use in the present invention is shown in FIG. 8, above.

The ATP core domain provides sufficient atomic weight and size to allow it, and analytes of interest bound to it, to avoid being retained by size-restricted sorbents used in the apparatus of versions of the present invention. The ATP core domain must be larger than the pore size of the size-restricted sorbent used in the stripping column. The core domain is preferably be a stable, non-degradable material such as silica or organic resin type nanoparticles. Preferably, the ATP core domain has a diameter larger than 10 nm, and preferably larger than 50 nm. Most preferably, the ATP core domain has a diameter between approximately 100 nm and approximately 200 nm.

Figure 10:
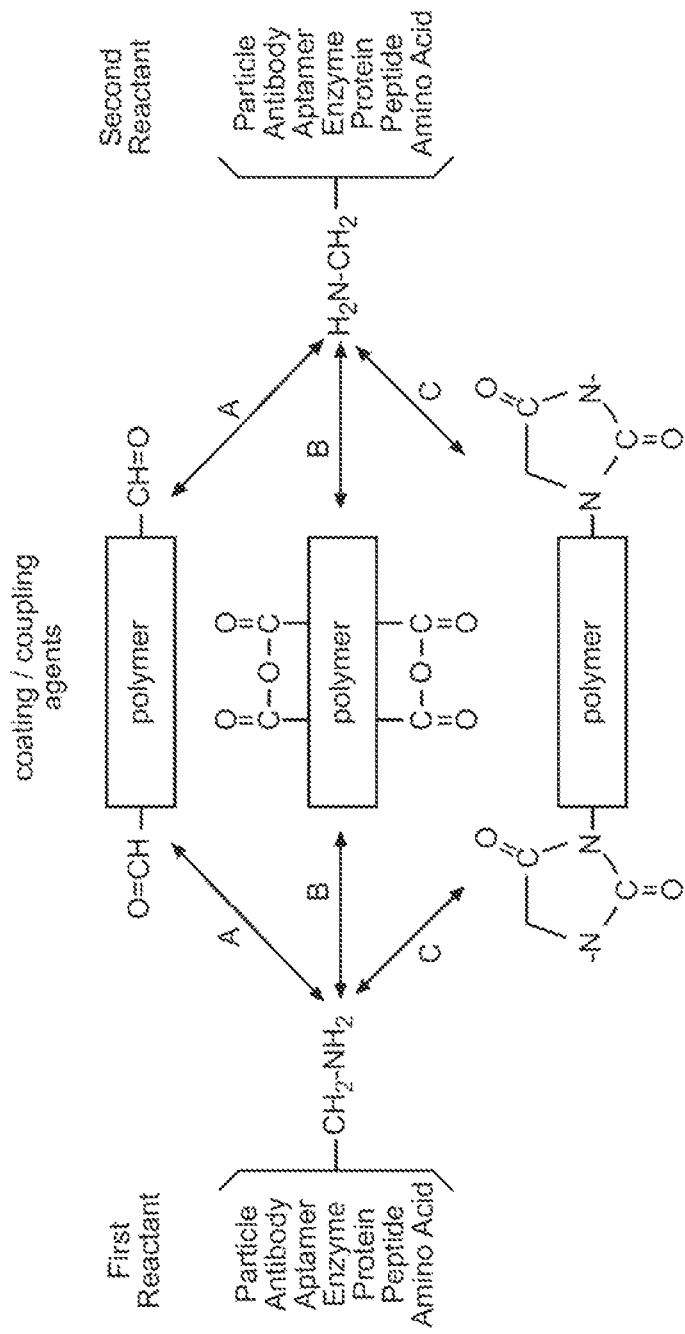
FIG. 10 is a diagram of one process for coating an ATP core domain with a binding domain in some embodiments of the present invention.

The ATP binding domain preferably coats all or substantially all of the core domain and is configured to specifically bind analytes of interest. The surfaces of suitable core domains such as nanoparticulate silica and organic resins may, if unmodified, non-specifically bind proteins. For such core domains, the core domain surface is substantially deactivated by coating the surface with a crosslinked organic polymer. The desired binding domain is then attached to this coating. Preferably, a binding domain comprises in part either a carbonyl group or a primary amine, or can be derivatized with a primary amine, as demonstrated in FIG. 10. Primary amines react readily with carbonyl groups to form a Schiff base, or with acid anhydrides to form an amide, or with succinimides to form an amide. Nanoparticles that contain multiple carbonyl groups are generally derived from the oxidation of polysaccharides by periodate oxidation of vicinal diols but carbonyl bearing polymers can also be obtained from the polymerization of carbonyl bearing acrylates. Reagents bearing multiple anhydride groups are generally derived from dehydration of a polyacrylic acid with dicyclohexyl carbodiimide. Polysuccinimide is generally prepared by heating aspartic acid in a vacuum to produce a polymer of approximately 20 kiloDaltons in molecular weight, which is then attached to a nanoparticle. The binding domain is, in some embodiments, attached to the core domain as shown in FIG. 10, depending on whether the binding domain involves multiple carbonyl groups (Reaction A of FIG. 10), polysaccharides (Reaction B of FIG. 10), or anhydride groups (Reaction C of FIG. 10). Residual reactive functional groups, such as carbonyl groups, in the binding domain are then destroyed by either reduction or reaction with a low molecular weight primary amino bearing substance such as ethanol amine, an amino acid, or an amine terminated polyoxyethylene. The binding domain thus binds selectively to analytes of interest based on one or more of their size, structure, and functional groups. Binding domains may include, for example, proteins, antibodies, avidin, protein A, protein G, polynucleotide aptamers, lectins, or imprinted polymers. In a preferred version hereof, the binding domain is an antibody, an aptamer, or a molecularly imprinted surface. Binding domains can be attached to the ATP core domain through a number of methods, as will be appreciated by one skilled in the art. In a preferred version hereof, the core domain is nanoparticulate silica and the binding domain is bound to the core domain by Schiff base coupling. Alternatively, core domain is a synthetic organic polymer and its outer surface comprises the binding domain.

If binding occurs between an ATP and an analyte of interest, that binding can comprise "specific" or "targeted" binding on the one hand, or "non-specific" or "non-targeted" binding on the other. Specific or targeted binding occurs when the analyte of interest comprises a class or category of sizes, structures, or functional groups to which the ATP binding domain is configured or selected to bind to or have affinity for, such that analytes of interest remain substantially bound to an ATP in the face of exposure to size-restricted sorbents, such as size-restricted sorbents with a reverse-phase interior portion, within desired ranges of temperature, pressure, and pH. Non-specific or non-targeted binding occurs when an agent does not comprise a class or category of sizes, structures, or functional groups to which the ATP binding domain is configured or selecting to bind to or have affinity for, but the agent weakly binds to the binding domain anyway. Exposure to a size-restricted sorbent should substantially disassociate non-specifically bound agents, but not specifically bound analytes of interest, from an ATP in favor of binding between those non-specifically bound agents and the sorbent.

One or more ATPs can be mixed with a sample within the scope and spirit of this invention in several different ways, as will be appreciated by one skilled in the art. One or more ATPs could be mixed into the sample at collection or in a collection container, such as a blood vial. One or more ATPs could be mixed into the sample after sub-component separation of a sample, such as through a PSD. For example, one or more ATPs could be mixed into a sample by adding the ATPs to a PSD as described above. The ATPs could be added before or after the PSD is used to collect and separate a sample, as will be appreciated by one skilled in the art. In other versions of the invention, ATPs could be mixed into a sample within the apparatus described herein at any point prior to introduction of the stripping column. For example, one or more ATPs could be mixed with a sample in an introductory mixing container fluidly connected to the apparatus, at the inlet port, at the inlet port as part of the sample introduction process, or at a secondary port between the inlet port of the apparatus and the stripping column. In these versions of the invention, the ATPs could be added in conjunction with the introduction of samples, or could be introduced into the apparatus at pre-defined intervals to mix with the samples via band spreading, as would be appreciated by one skilled in the art. In a preferred version of the present invention, samples are being introduced to the apparatus continuously or on a continuous interval basis, and one or more ATPs are also being introduced into the apparatus on a continuous or continuous interval basis, by way of, for example, a pump. In another version, ATPs are added continuously to an aqueous buffer that moves through the apparatus and comprises, at various points, the mobile phase of the stripping column and the mobile phase of the enriching column. In these versions, the sample mixture can be added as in normal LC.

As would be appreciated by one skilled in the art, one ATP may target a single analyte or multiple analytes, and the methods and apparatuses described herein may employ a single ATP or multiple ATPs. For example, in a version where the binding domain of the ATP comprises a polyclonal antibody targeted at a particular protein, that ATP could bind all the proteoforms of the protein. Versions of the present invention can use one ATP or can use multiple ATPs sequentially or simultaneously to target multiple analytes of interest, so long as the total number of agents targeted by the one or more ATPs can be reasonably analyzed simultaneously by MS, as will be appreciated by one skilled in the art.

The apparatus of versions of the present invention comprises a structure for introducing samples such as an inlet port (1) or a mixing chamber, at least one stripping column (3), optionally, a disassociating portion (5), and, optionally, at least one enriching column (7). The structure for introducing samples can be any structure for introducing an agent to a system. For example, the structure for introducing samples can, within versions of the present invention, comprise a port, an opening, a valve, or a pumping system.

The apparatus in its versions further comprises one or more stripping columns (3). A stripping column (3) comprises at least a mobile phase, a stationary phase, and a container for containing the mobile phase and stationary phase. The mobile phase is an LC-appropriate solvent or aqueous buffer, as will be appreciated by one skilled in the art. In a preferred version, the mobile phase is an aqueous physiological buffer with a pH of approximately 7 to 8, such as a phosphate buffer. Mobile phase can be pushed through the stripping column (3) using gravity or positive pressure, including pumps (9). The mobile phase can be pushed through the stripping (3) column at various speeds, depending on whether the desired outcome is to maximize throughput or to maximize time of contact with the stationary phase. In preferred versions hereof, the linear velocity of mobile phase through stripping column container would be in the range from 1 mm/sec to 1 cm/sec, and the internal diameter of the stripping column container would range from 100 um to 4.6 mm. Column diameter is varied to accommodate difference in required loading capacity to deal with sample size, where the loading capacity of columns increases with the square of the radius, as would be appreciated by one skilled in the art.

The stationary phase of the stripping column (3) comprises a size-restricted sorbent on a solid, insoluble matrix. As will be appreciated by one skilled in the art, the amount of stationary phase within the stripping column is a function of the internal surface area of the size-restricted sorbent, the pore size of the size-restricted sorbent, the makeup of the mobile phase, the intended flow speed of the mobile phase and the size of the container comprising the stripping column. In versions of the present invention, the stationary phase is prepared by silylating the surface of a silica particle core domain with gamma-aminopropyl trimethoxysilane followed by derivatization of the derived primary amine surface with either octanoic or butanoic acid.

The size-restricted sorbent generally comprises a bed of particles, each particle comprising an inactive (that is, non-adsorbing) external portion, an active (that is, adsorbing) internal portion, and a pore providing access from the inactive external portion to the active internal portion. As will be appreciated by one skilled in the art, the inactive external portion is configured to be insoluble in the mobile phase, and is further configured not to substantially bind to ATPs or to analytes specifically bound to ATPs, or to targeted functional groups of those analytes. In some versions of the invention, the external portion will be a non-chelating substance. In other versions of the invention, the external portion will be a hydrophobic substance. In a preferred version of the invention, the external portion is a hydrophilic sub stance.

The active internal portion of the size-restricted sorbent particle is configured to bind to agents that are able to pass through the pore—that is, generally, to substances not specifically bound to the binding domain of an ATP. In some versions of the invention, the internal portion will comprise one or more chelating substances. In other versions the internal surface will comprise a phenyl boronic acid that captures vicinyl diols. In still other versions of the invention, the internal portion will comprise a hydrophilic substance. In still other versions of the invention, the internal portion will be a structure-specific adsorbing agent such as an antibody, aptamers, lectin, or a molecularly imprinted surface. In a preferred version of the invention, the internal portion is a hydrophobic substance.

In a preferred version hereof, a size-restricted sorbent is synthesized as follows: Substance B shown in FIG. 8 herein is contacted with 25 um silica particles of at least 10 nm, and preferably 50 nm, pore diameter (product "C", FIG. 8). The nanoparticles are too large to enter pores in the 25 um silica, thus only the outside of the sorbent is coated. Residual primary amines inside the sorbent particle are then derivatized with butyric or octanoic acid, as will be appreciated by one skilled in the art, to create an internal reversed phase surface.

Within the stripping column (3), substances in the mobile phase, specifically including the complex formed by an ATPs and analytes of interest bound to the ATP binding domain, will encounter the inactive external portion of the size-restricted sorbent and not bind to it or be substantially retained by it. Access to the active internal portion is provided through pores in the size-restricted sorbent particles. The pore size is selected to only allow agents, compounds, or complexes of a certain maximum size to enter the pore and encounter the active inner portion. Thus, complexes above that size, such as the ATP-analyte of interest complex, pass through the stationary phase encountering only the inactive external portion, and thus are not meaningfully retained by the size-restricted sorbent. Pore size is ideally selected to be generally larger than biological compounds or agents not bound to an ATP, but smaller than the size of an ATP. In some versions of the invention, the pore size may be approximately 10 nm. In other versions of the invention, the pore size may range from 10 nm to 20 nm. In a preferred version of the invention, the pore size is in a range from approximately 30 nm to approximately 100 nm. As will be appreciated by one skilled in the art, analytes of interest, such as protein complexes, with an atomic weight of approximately $10^6$ daltons can penetrate a pore with a diameter in the 30 nm to 100 nm range and be adsorbed by the active internal portion.

In this way, the complex formed between an ATP and an analyte of interest is subjected to size-based exclusion mechanism as it passes through the stripping column, with the ATP-analyte of interest complex not being retained and moving on to later states of separation and analysis. Unbound and weakly bound biological agents are retained by the stripping column stationary phase. The size exclusion separation of versions of the present invention is rapid compared to traditional affinity chromatography separation. As will be appreciated by one skilled in the art, agents and compounds not targeted by an ATP, but with affinity to the active internal portion of the size-restricted sorbent, will have multiple encounters with size-restricted sorbent particles during transit through the stripping column (3), and substantially all of these non-targeted agents and compounds will pass through the pores in the size-restricted sorbent and be retained by the active internal portion of the size-restricted sorbent. Since the affinity between the ATP and the targeted analytes will generally exceed the affinity between the internal active portion and the targeted analytes, targeted analytes specifically bound to an ATP will substantially remain so bound during passage through the stripping column (3), and the ATP-analyte complex will be too large to pass through the pores of the size-restricted sorbent to encounter the active internal portion. Agents non-specifically bound to ATPs will experience greater affinity with the active internal portion, and will substantially disassociate from ATPs to bind to and be retained by the size-restricted sorbent. Passage of the sample mixture through the stripping column (3) will substantially strip from the mobile phase all agents except for analytes of interest specifically bound to ATPs, as well as ATPs themselves (whether or not bound to an analyte). Also remaining in the mobile phase will be very large compounds, such as large natural compounds, and impurities without affinity for an ATP or for the active internal portion of the stationary phase. The number of unique compounds remaining in the mobile phase will, however, be reduced, enhancing the feasibility of MS or other analytical techniques. As will be appreciated by one skilled in the art, passage of a sample mixture through the stripping column (3) in connection with suitable ATPs substantially reduces the number of unique agents remaining in the mobile phase to a number upon which analysis, preferably MS, can be fruitfully performed. In versions of the present invention, the output of the stripping column (3) includes an enriched suspension of ATP-analyte of interest complex.

The apparatus of the present invention may comprise a single stripping column (3) or multiple stripping columns working in parallel or sequentially. The stripping column (3) portion of the apparatus may further include a switching valve (11) to direct flow from the inlet port (1) of the apparatus to one or more selected stripping columns and to shut off flow to other selected stripping columns. In a preferred version of the invention, there are two stripping columns (3) and a switching valve (11) configured to operate such that sample flow from the inlet port (1) is directed to a first stripping column, and while the first stripping column is being loaded with sample, a second stripping column is eluting to the disassociating portion of the apparatus. The switching valve (11) can then be switched to load the second column while the first column elutes. Optionally, each stripping column (3) may further be operatively connected to a pump (9) to assist with elution. In this way, a relatively continuous flow of sample can be maintained through the apparatus.

The apparatus may optionally include an additional port, pump, or other structure to allow the addition of derivatizing, or digesting agents in the stripping column, after the stripping column but before the disassociating portion, or, in the disassociating portion. Such added agents will, as will be appreciated by one skilled in the art, mix with analytes of interest primarily through band spreading. In a preferred version hereof, a pump is disposed between the stripping column and the disassociating portion to allow the selective, interval-based, or continuous addition of the digesting agent trypsin to the enriched sample mixture. As will be appreciated by one skilled in the art, digestion or derivatization can result in more efficient or more sensitive detection of certain analytes of interest within the scope and spirit of this invention by MS, such as in proteomics.

A disassociating portion (5) preferably is fluidly connected to the stripping column portion (3). The disassociating portion (5) preferably comprises a container configured primarily to disassociate analytes of interest from the ATPs to which they are bound by hosting conditions favorable to such disassociation. In a preferred version hereof, the disassociating portion (5) continuously disassociates ATPs from analytes of interest as the sample mixture passes through the disassociating portion (5). In embodiments of the invention in which derivatizing or digesting agents are added after the stripping column (3) or in the disassociating portion (5), these agents will substantially interact with analytes of interest in the disassociating portion (5) after such analytes of interest are disassociated from ATPs. Optionally, the disassociating portion (5) may comprise a sample plate such as a MALDI sample plate or a microtiter plate. In these embodiments of the invention, such a plate is not fluidly connected to a stripping column (3), but is used to collect outflow from a stripping column (3). Conditions favorable for disassociation may be created or maintained within the MALDI or microtiter plate by any means known to the art. In this embodiment, a disassociating agent is added to the plate comprising a dissociating portion (5) and MS analysis can be performed without further processing of the sample mixture, and specifically without undergoing the enrichment column step described elsewhere herein.

Conditions favorable for disassociation include raising temperature to above 50 degrees Celsius, and preferably to above 70 degrees Celsius. Raising temperature can be accomplished by, for example, providing an oven or heating element in operative connection with the disassociating portion (5). Conditions for disassociation also include lowering the pH of solution to approximately 4 or below, and preferably to 3 or below. Lowering pH can be accomplished by, for example, addition of glycine:HCl. As will be appreciated by one skilled in the art, a variety of other conditions would be favorable for disassociation, depending on the specific identifies of the mobile phase solvent, ATP, and analyte of interest, and are within the scope and spirit of this invention.

Optionally and preferably, the disassociating portion (5) further separates disassociated ATPs from analytes of interest through a tubular pinch effect, in which, in certain configurations of container, large particles such as ATPs are pinched into higher velocity segments of the laminar flow of the mobile phase and thus exit the disassociation portion (5) prior to the disassociated analytes of interest. The tubular pinch effect can also facilitate mixing of digesting agents, derivatizing agents, or other agents added between a stripping column (3) and a disassociating portion (5) or within a disassociating portion (5).

The tubular pinch effect is observed in tubes with interior diameters equal to or less than approximately 100 um, as well as in packed particle beds with channels of appropriate size between the particles in the bed. Mobile phase passing through these channels passes in a laminar flow profile, which, through the tubular pinch effect, focuses submicron particles into streams. In a preferred embodiment hereof, there is a valve, port, or other structure between the disassociating portion (5) and the enriching column (7), or within the enriching column (7), to facilitate removal of bands of mobile phase containing primarily disassociated ATPs separated through the tubular pinch effect.

In a preferred embodiment hereof, the disassociating portion (5) comprises a 100 um diameter open tubular quartz capillary of 10-100 cm in length with a neutral, hydrophilic internal coating.

Versions of the present invention optionally include at least one enriching column (7) in fluid connection with the disassociating portion (5). The enriching column (7) separates analytes from disassociated ATPs, allowing relative enrichment and band focusing of the analytes of interest. The enriching column (7) may further allow relative enrichment of analytes by facilitating separation of impurities. As will be appreciated by one skilled in the art, a large variety of LC methods known to the art are available and can be used in the enriching column (7) within the scope and spirit of this invention.

The enriching column (7) comprises a container (13), a mobile phase, and a stationary phase. The enriching column container (13) is configured to host, and hosts, conditions favorable to prohibiting reassociation of analytes of interest with ATPs subsequent to passage through the disassociating portion (5). As will be appreciated by one skilled in the art, a variety of methods and means can be used, depending on the conditions selected in the disassociating portion, to maintain disassociation of analytes of interest from ATPs. For example, pH of less than approximately 4, or preferably less than approximately 3, may be maintained without further action within the enriching column (7) if such pH was established in the disassociating portion (5). For separate example, where the pH of solution was lowered in the disassociating portion (5), the pH may be lowered further still in the enriching column (7), preferably through addition of glycine:HCl. For yet another example, where pH of solution was not lowered in the disassociating portion (5), pH may be lowered in the enriching column (7), preferably by addition of glycine:HCl. As will be appreciated by one skilled in the art, the enriching column (7) may, within the scope and spirit of this invention, include a port or other structure allow access for the introduction of additional reagents. In a preferred embodiment hereof, the enriching column (7) is further operative connection with a heating element (15) to create a temperature within the enriching column (7) above 50 degrees Celsius, and most preferably above 70 degrees Celsius. Optionally, the function of the enriching column may occur within a portion of the stripping column, provided the stripping column further includes a disassociating means to disassociate analytes of interest from ATPs prior to enrichment.

The mobile phase of the enriching column (7) is an LC-appropriate solvent, as will be appreciated by one skilled in the art. In a preferred embodiment, the mobile phase is an aqueous buffer, and, in a most preferred version, is predominately the same aqueous buffer used to carry sample through the stripping column (3) and the disassociating portion (5). Thus, in this most preferred embodiment, the term "mobile phase" can be used to refer to the solvent or buffer carrying the sample at virtually any point in the method or any location in the apparatus.

The mobile phase can be pushed through the enriching column (7) using gravity or positive pressure, including a pump (9) or pumps. Positive pressure may be generated by a pump (9) or pumps located within the apparatus in operative connection at least one of the stripping column (3), the disassociating portion (5), and the enriching column (7). Mobile phase can be pushed through the enriching column (7) at various selected speeds, depending on whether the desired outcome is to maximize throughput or to maximize time of contact with the stationary phase within the enriching column (7). In general, desirable flow speed within the enriching column (7) is determined as a function of the loading kinetics of the stripping column (3). Preferably, the flow speed of mobile phase within the enriching column (7) is substantially the same as the flow speed of mobile phase within the stripping column (3).

The stationary phase of the stripping column (3) is supported on a solid, insoluble matrix. The stationary phase of the enriching column (7) may comprise any of a large variety of stationary phases suitable for LC, including specifically and preferably organic phases used in LC. The enriching column (7) may include a stationary phase comprising, for example, hydrocarbons, fatty acids, antibodies, aptamers, lectins, or molecularly imprinted polymers.

Preferably, the stationary phase of the enriching column (7) is both appropriate for chromatographic separation of analytes of interest preparatory for MS and is suitable for use at substantially the same flow rate used in the stripping column (3). The enriching column (7) stationary phase may, for example, comprise a size-restricted sorbent identical to that used in the stripping column (3).

Embodiments of the apparatus invention including an enriching column (7) may comprise a single enriching column or multiple enriching columns working in parallel or sequentially. The enriching column (7) may further be connected fluidly to a second switching valve (17) to direct flow from the disassociating portion (5) of the apparatus to one or more selected enriching columns and to shut off flow to other selected enriching columns. Preferably, there are two enriching columns and a second switching valve (17) directing sample flow from the disassociating portion (5) to a first enriching column while a second enriching column is eluting for MS analysis, and then switching to provide sample flow to the second enriching column while the first enriching column is eluting for MS. In this way, a near-continuous flow of sample can be maintained.

Optionally, the enriching column may be operatively coupled to an outflow valve (19) with two settings. In a first setting, the outflow valve (19) directs outflow from the enriching column or columns to waste. Due to the tubular pinch effect described above, the first portion of the elution in each sample mixture band may comprise predominately, and possibly exclusively, ATPs disassociated from analytes. It is this first portion of elution that is directed to waste. In its second setting, the outflow valve (19) directs outflow from the enriching column or columns to an analytical device, preferably a mass spectrometer, and a mobile phase gradient is pumped through the column, causing enriched analytes to be eluted for MS analysis. In a preferred embodiment, the outflow valve (19) is placed in its first setting while the first portion of elution flows through it, and then is changed to its second setting after the first portion of elution has substantially passed. As will be appreciated, an outflow valve (19) may be used in similar fashion in embodiments lacking an enrichment column (7), such as, for example, by connecting an outflow valve (19) to a disassociating portion or portions.

The enriching column may optionally be fluidly connected to one or more receiving containers configured to store sample that has undergone the multi-dimensional separation within the apparatus, such sample being substantially prepared for MS analysis. The enriching column may alternatively be operatively connected directly to an MS input to facilitate continuous MS analysis as sample continuously flows from the apparatus.

One of the major distinctions between the methods and apparatuses described herein and methods known to the art are that the affinity chromatographic sorbents taught herein are 10 nm to 100 nm in size, not 1 um to 50 um as known to the prior art. Further, the methods described herein have the advantages of affinity-based chromatography, however, since the primary separation is size-based rather than affinity based, the methods described herein can be completed as much as 10 times more quickly at a given mobile phase velocity than affinity LC separations known to the art.

Figure 6:
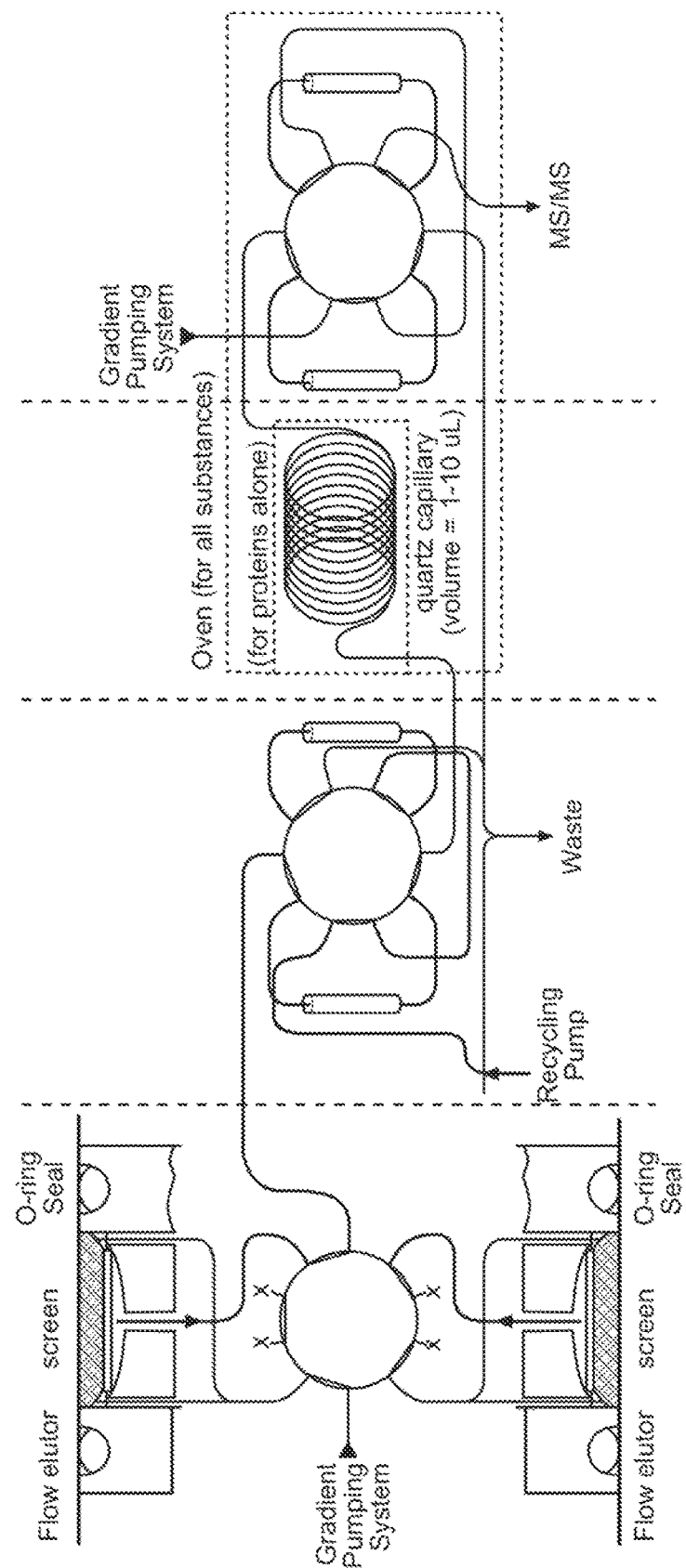
FIG. 6 is a block diagram illustrative of one embodiment of an apparatus according to and for practicing the present invention.
Figure 7:
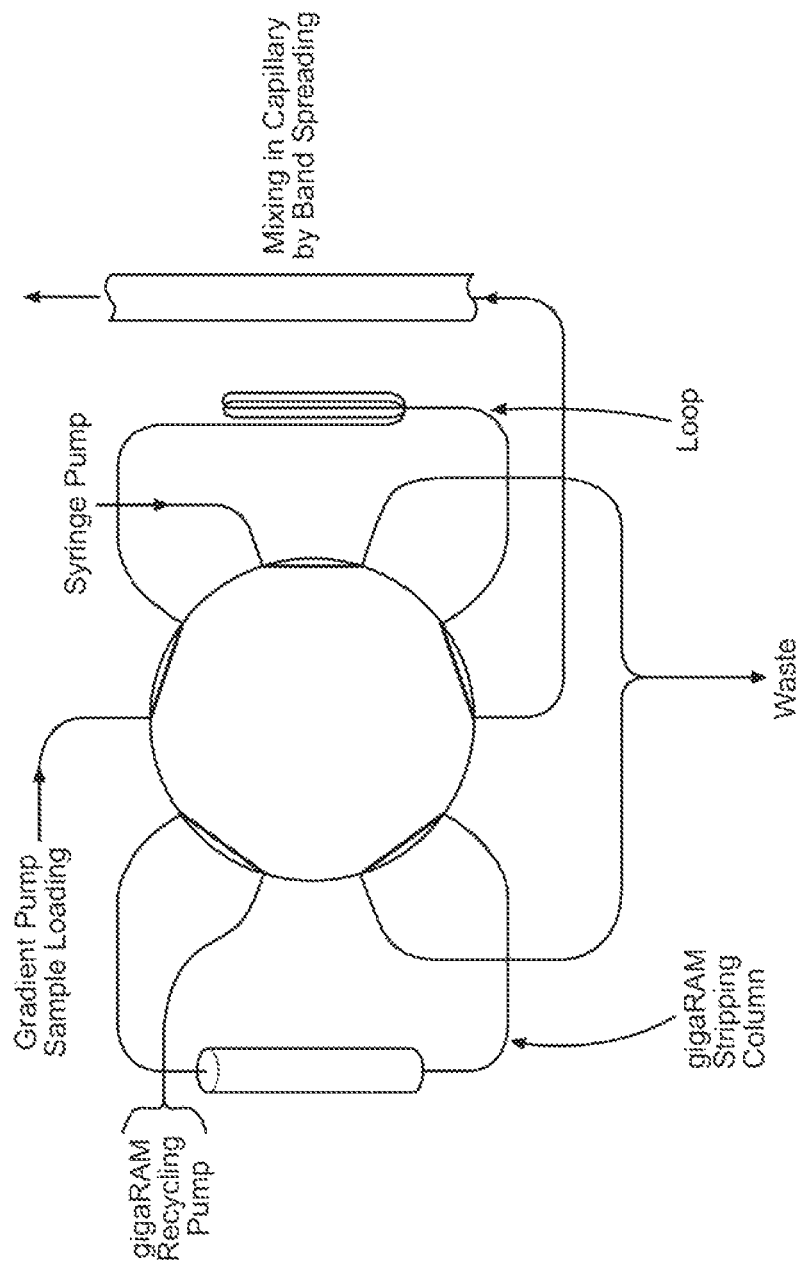
FIG. 7 is a block illustrative diagram of a stripping column portion adapted to add trypsin to said sample as it moves to said disassociating portion in a version of the present invention.

For example, and referring now to FIGS. 6 and 7, in one embodiment an apparatus taught by the present invention may include an inlet port (1) that comprises a pair of selectively operable flow elutors (21), a pair of screens (23), and a pair of O-ring seals (25) operatively connected to a selectively operable first gradient pumping system (27); a stripping column portion comprising a central stripping container (29), a pair of selectively operable stripping columns (3), a recycling pump (31), a first switching valve (13), and a first waste outlet (33); a disassociating portion (7) comprising a quartz capillary with a volume of 1 to 10 uL and contained within an oven heating element (15); and an enriching portion comprising an enriching portion central container (35), a second switching valve (17), a pair of selectively operable enriching columns (13) operatively connected to a selectively operable second gradient pumping system (37), an outflow valve (19), and, as shown in FIG. 7, optionally a second waste outlet (39).

Thus, specific methods of rapidly and efficiently qualitatively and quantitatively analyzing analytes of interest from a whole biological sample, and apparatuses for the same, have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A method of qualitatively and qualitatively analyzing samples of biological fluid, said method comprising the steps of:
    (a) providing a sample for analysis;
    (b) selecting at least one ATP, each said ATP comprising a core domain and a binding domain, wherein said binding domain is selected to bind to one or more functional groups associated with analytes of interest;
    (c) adding a quantity of said at least one ATP to a plasma separation device;
    (d) adding said sample to said plasma separation device to create a sample mixture;
    (e) providing conditions suitable for analytes of interest present in said sample to bind to said at least one ATP;
    (f) loading said sample mixture into an apparatus for analysis, said apparatus comprising at least one stripping column, at least one disassociating portion fluidly connected to said stripping column, and at least one enriching column fluidly connected to said disassociating portion;
    wherein said stripping column comprises a first chromatography column, wherein said first chromatography column is a size-exclusion chromatography column with a first mobile phase and a first stationary phase, wherein said first stationary phase is configured to exclude particles or complexes larger than 30 nm in diameter, and said first mobile phase comprises a solvent;

wherein said disassociating portion comprises at least one container; and wherein said enriching column comprises a second chromatography column comprising a second stationary phase and a second mobile phase, said second stationary phase comprises a least one sorbent selected to induce chromatographic separation in the analytes of interest, and said second mobile phase comprises a solvent;

(f) moving said sample mixture through said at least one stripping column within said first mobile phase at a first rate;

(g) establishing conditions said at least one disassociating portion suitable to substantially disassociate said analytes of interest from said at least one ATP;

(h) moving said sample mixture through said disassociating portion at a second rate, said second rate selected to allow substantially all of said analytes of interest to disassociate from said at least one ATP;

(i) establishing conditions in said at least one enriching column suitable to substantially prevent rebinding of said analytes of interest to said at least one ATPs;

(j) moving said sample mixture through said enriching column within said second mobile phase at a third rate, said third rate selected to allow chromatographic separation of analytes of interest; and (h) analyzing elution from said enriching column to determine the presence or relative amount of analytes of interest.

2. The method of claim 1, wherein said plasma separation device is pre-loaded with one or more internal standards.

3. The method of claim 2, wherein said one or more internal standards are added to said sample mixture.

4. The method of claim 1, wherein said plasma separation device is pre-loaded with one or more derivatizing agents.

5. The method of claim 4, wherein said one or more derivatizing agents are added to said sample mixture.

6. The method of claim 1, wherein said plasma separation device is pre-loaded with one or more digesting agents.

7. The method of claim 6, wherein said one or more digesting agents are added to said sample mixture.

8. The method of claim 6, wherein at least one of said one or more digesting agents comprises trypsin.

9. The method of claim 1, wherein said plasma separation device is pre-loaded with one or more ATPs.

10. The method of claim 9, wherein said one or more ATPs are added to said sample mixture.

* * * * *